(12) United States Patent
Sano

(10) Patent No.: US 8,858,452 B2
(45) Date of Patent: Oct. 14, 2014

(54) CHECK VALVE STRUCTURE, DIAPHRAGM PUMP, AND SPHYGMOMANOMETER

(75) Inventor: Yoshihiko Sano, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 692 days.

(21) Appl. No.: 12/937,548

(22) PCT Filed: Apr. 10, 2009

(86) PCT No.: PCT/JP2009/057323
§ 371 (c)(1),
(2), (4) Date: Oct. 13, 2010

(87) PCT Pub. No.: WO2009/128394
PCT Pub. Date: Oct. 22, 2009

(65) Prior Publication Data
US 2011/0028853 A1   Feb. 3, 2011

(30) Foreign Application Priority Data

Apr. 16, 2008  (JP) ................ 2008-106821

(51) Int. Cl.
| | | |
|---|---|---|
| *A61B 5/0235* | (2006.01) | |
| *F16K 15/00* | (2006.01) | |
| *F04B 43/00* | (2006.01) | |
| *A61B 5/021* | (2006.01) | |
| *F16K 15/16* | (2006.01) | |
| *F16K 15/14* | (2006.01) | |
| *F04B 53/10* | (2006.01) | |

(52) U.S. Cl.
CPC .......... *A61B 5/0235* (2013.01); *F04B 43/0045* (2013.01); *A61B 5/02141* (2013.01); *F16K 15/16* (2013.01); *F16K 15/148* (2013.01); *F04B 53/1037* (2013.01)

USPC .......... 600/490; 600/481; 600/485; 137/511; 137/512; 137/512.15

(58) Field of Classification Search
USPC ............. 600/490–499; 137/511, 512, 512.15; 417/244, 44.9, 395, 413.1, 560, 566
See application file for complete search history.

(56) References Cited

U.S. PATENT DOCUMENTS 4,801,249 A * 1/1989 Kakizawa ............... 417/269
5,332,370 A * 7/1994 Nakayama et al. ....... 417/413.1
(Continued)

FOREIGN PATENT DOCUMENTS

DE  10 2006 061 760 A   4/2008
EP   1 308 622 A         5/2003
(Continued)

OTHER PUBLICATIONS

Boothroyd et al. "Product Design for Manual Assembly." Product Design for Manufacture and Assembly. 1994. 61 pages.*

(Continued)

*Primary Examiner* — Navin Natnithithadha
*Assistant Examiner* — Meredith Weare
(74) *Attorney, Agent, or Firm* — Osha Liang LLP

(57) ABSTRACT

A check valve structure has a first space and a second space. The check valve structure is configured to allow a flow of a fluid from the first space to the second space and to inhibit flow of the fluid from the second space to the first space. The check valve structure has a partition wall arranged between the first space and the second space and provided with a communication hole providing communication between the first space and the second space, an elastic film body for covering the side of the second space of the communication hole so as to prevent a reverse flow of the fluid, an elastic member having a wall portion surrounding the communication hole for holding the elastic film body, and a nipping member for nipping the elastic member with the partition wall.

15 Claims, 12 Drawing Sheets

(56) References Cited

U.S. PATENT DOCUMENTS

| | | | |
|---|---|---|---|
| 5,476,367 A | 12/1995 | Zimmermann et al. | |
| 5,570,694 A * | 11/1996 | Rometsch | 600/493 |
| 6,158,971 A * | 12/2000 | Takagi | 417/244 |
| 6,382,928 B1 * | 5/2002 | Chang | 417/269 |
| 6,843,643 B2 * | 1/2005 | Fukami et al. | 417/413.1 |
| 7,040,876 B2 * | 5/2006 | Fukami et al. | 417/413.1 |
| 7,527,595 B2 * | 5/2009 | Hori | 600/498 |
| 7,819,636 B2 * | 10/2010 | Huang | 417/269 |
| 2002/0051717 A1 * | 5/2002 | Fukami | 417/420 |
| 2005/0049513 A1 * | 3/2005 | Hori | 600/498 |
| 2005/0169780 A1 * | 8/2005 | Fukami et al. | 417/413.1 |
| 2006/0025693 A1 * | 2/2006 | Sano et al. | 600/490 |
| 2007/0140879 A1 * | 6/2007 | Huang | 417/472 |

FOREIGN PATENT DOCUMENTS

| | | |
|---|---|---|
| EP | 1 555 469 A | 7/2005 |
| JP | 51-9510 | 1/1976 |
| JP | 59-44949 A | 3/1984 |
| JP | 59-44959 A | 3/1984 |
| JP | 61-294270 A | 12/1986 |
| JP | 62-092373 U | 6/1987 |
| JP | 4-34947 A | 2/1992 |
| JP | 6327640 A | 11/1994 |
| JP | 7-112749 A | 5/1995 |
| JP | 10-13186 A | 1/1998 |
| JP | 10-20647 A | 1/1998 |
| JP | 10-29647 A | 2/1998 |
| JP | 10-131862 A | 5/1998 |
| JP | 11-218244 A | 8/1999 |
| JP | 11324927 A | 11/1999 |
| JP | 2002-005029 A | 1/2002 |
| JP | 2002062207 A | 2/2002 |
| JP | 2003-139258 A | 5/2003 |
| JP | 2003-269337 A | 9/2003 |
| JP | 2004-225812 A | 8/2004 |
| JP | 2005-201279 A | 7/2005 |
| JP | 2006029284 A | 2/2006 |

OTHER PUBLICATIONS

International Search Report w/translation from PCT/JP2009/057323 dated Jul. 21, 2009 (4 pages).
Patent Abstracts of Japan; Publication No. 10-029647 dated Feb. 3, 1998 (1 page).
Patent Abstracts of Japan; Publication No. 07-112749 dated May 2, 1995 (1 page).
Patent Abstracts of Japan; Publication No. 2004-225812 dated Aug. 12, 2004 (1 page).
Patent Abstracts of Japan; Publication No. 61-294270 dated Dec. 25, 1986 (1 page).
Patent Abstracts of Japan; Publication No. 2005-201279 dated Jul. 28, 2005 (1 page).
Patent Abstracts of Japan; Publication No. 59-044959 dated Mar. 13, 1984 (1 page).
Patent Abstracts of Japan; Publication No. 04-034947 dated Feb. 5, 1992 (1 page).
Patent Abstracts of Japan; Publication No. 10-131862 dated 0511911998 (1 page).
Patent Abstracts of Japan; Publication No. 2003-139258 dated May 14, 2003 (1 page).
Patent Abstracts of Japan; Publication No. 11-218244 dated Aug. 10, 1999 (1 page).
Patent Abstracts of Japan; Publication No. 2003-269337 dated Sep. 25, 2003 (1 page).
Patent Abstracts of Japan; Publication No. 2002-005029 dated Jan. 9, 2002 (1 page).
Patent Abstracts of Japan; Publication No. 11-199618 dated Jul. 27, 1999 (PAJ for JP10-013186A) (1 page).
Patent Abstracts of Japan; Publication No. 10-020647 dated Jan. 23, 1998 (1 page).
Office Action issued by German Patent and Trade Mark Office on Jan. 22, 2013 in Application No. 11 2009 000 908.5 (13 pages).
Japanese Office Action Issued in Japanese Application No. 2008-106821, Dated Jul. 10, 2012 (11 Pages With English Translation).
English Patent Abstract of JP 2006-029284, Publication Date: Feb. 2, 2006 (1 Page).
English Patent Abstract of JP 2002-062207, Publication Date: Feb. 28, 2002 (1 Page).
English Patent Abstract of JP 11-324927, Publication Date: Nov. 26, 1999 (1 Page).
English Patent Abstract of JP 11-327640, Publication Date: Nov. 26, 1999 (1 Page).

* cited by examiner

CHECK VALVE STRUCTURE, DIAPHRAGM PUMP, AND SPHYGMOMANOMETER

TECHNICAL FIELD

The present invention relates to a check valve structure, a diaphragm pump, and a sphygmomanometer.

BACKGROUND ART

Recently, self-management of blood pressure is increasingly regarded as important, and a domestic use sphygmomanometer is widely used. In time of measuring the blood pressure, an arm band in which an air bladder is incorporated is wound around part of a living body, and the air is fed into the air bladder so as to pressurize the air bladder. The blood pressure is measured from artery information obtained by compressing the living body. An air pump is used for pressurizing the air bladder. The air pump is provided with a rubber diaphragm forming a pump chamber in a case, and performs a pump operation by a capacity change of the diaphragm. Check valves are installed in the air pump so that the discharged air and the suctioned air do not flow reversely to each other. A thin-film shape rubber material is generally used as the check valves.

The thin-film shape valve serving as a discharge valve has a structure in which the valve is opened by discharge pressure so as to feed the air into an adjacent air chamber, and the valve is closed in time of suctioning the air so that the air is not returned in the reverse direction. The thin-film shape valve serving as a suction valve has a structure in which the valve is opened by suction pressure (minus) so as to suction the air into the pump chamber, and the valve is closed in time of compressing so that the air is not leaked. In general, a shape of the thin-film shape valves includes a cylindrical shape, a thin-film leaf shape, and an umbrella shape. Conventionally, there are various technologies proposed for a thin-film shape check valve and a pump using the check valve (for example, refer to Japanese Unexamined Patent Publication No. 10-131862 (patent document 1), Japanese Unexamined Patent Publication No. 11-218244 (patent document 2), Japanese Unexamined Patent Publication No. 2003-139258 (patent document 3), Japanese Unexamined Patent Publication No. 2002-5029 (patent document 4), and Japanese Unexamined Patent Publication No. 2003-269337 (patent document 5)).

In a small pump described in Japanese Unexamined Patent Publication No. 10-131862 (patent document 1), a cylindrical discharge valve is provided in a center part between a plurality of diaphragms, and suction valves are respectively provided for the diaphragms, so that the central cylindrical valve is sealed in a taper shape to prevent air leakage. A discharge valve and a suction valve described in Japanese Unexamined Patent Publication No. 11-218244 (patent document 2) are formed into an umbrella shape, and ribs are provided in an outer circumference so as to prevent the air leakage from film ends. In a check valve described in Japanese Unexamined Patent Publication No. 2003-139258 (patent document 3), convex portions or concave portions are provided in a discharge valve and a suction valve and fitted to each other, so that positioning is performed and liftup is prevented to prevent the air leakage.

In a small pump described in Japanese Unexamined Patent Publication No. 2002-5029 (patent document 4), a suction hole is formed in a drive body connected to a bottom part of a diaphragm, and a thin-film shape suction valve is provided in the bottom part of the diaphragm. In a diaphragm pump described in Japanese Unexamined Patent Publication No. 2003-269337 (patent document 5), a suction valve is formed into a thin-film shape or a leaf shape, a plurality of the suction valves and a plurality of diaphragms are integrated, and convex portions surrounding suction ports are provided on lower surfaces of the suction valves so as to prevent the air leakage.

Patent Document 1: Japanese Unexamined Patent Publication No. 10-131862
Patent Document 2: Japanese Unexamined Patent Publication No. 11-218244
Patent Document 3: Japanese Unexamined Patent Publication No. 2003-139258
Patent Document 4: Japanese Unexamined Patent Publication No. 2002-5029
Patent Document 5: Japanese Unexamined Patent Publication No. 2003-269337

SUMMARY OF THE INVENTION

With the small pump described in Japanese Unexamined Patent Publication No. 10-131862 (patent document 1), it is highly difficult to insert and assemble the soft thin-film shape cylindrical valve into a hole portion in time of assembling the pump, and a shape of the valve is complicated. With the umbrella valves described in Japanese Unexamined Patent Publication No. 11-218244 (patent document 2), an O ring sealing property of umbrella attachment portions is insufficient, and there may be insufficiencies in stability and durability after attachment. With the check valve described in Japanese Unexamined Patent Publication No. 2003-139258 (patent document 3), there are the same number of suction valves as a plurality of diaphragms, so that the number of parts and assembling manhour are increased.

With the small pump described in Japanese Unexamined Patent Publication No. 2002-5029 (patent document 4), the valve is provided in the drive body connected to the bottom part of the diaphragm. Thus, the drive body is actuated in time of driving the pump, and the coupled valve is actuated together with the drive body, so that valve deformation is large and the air leakage is easily generated. The diaphragm pump described in Japanese Unexamined Patent Publication No. 2003-269337 (patent document 5) has a characteristic that the suction valves are integrated with the diaphragms so as to reduce the number of parts. However, since there is no configuration to hold down peripheries of the valves, the valves are easily deformed in time of assembling, and the air leakage is easily generated.

One or more embodiments of the present invention provides a check valve structure capable of suppressing deformation of a thin-film shape check valve due to distortion in time of assembling, actuating a pump, or the like, and suppressing a decrease in pump efficiency due to air leakage caused by a change in close attachment states of a hole through which the air flows in time of operating the pump. One or more embodiments of the present invention provides a diaphragm pump provided with the above check valve structure, and a sphygmomanometer provided with the diaphragm pump.

A check valve structure according to one or more embodiments of the present invention is a valve structure including one check valve for allowing a flow of a fluid from a first space to a second space and inhibiting a flow in the reverse direction thereof, and another check valve for allowing a flow of the fluid from another first space to another second space and inhibiting a flow in the reverse direction thereof. The check valve structure includes a partition wall arranged between the first space and the second space and between the another first space and the another second space and provided with a communication hole providing communication between the first space and the second space and another communication hole providing communication between the another first space and the another second space. An elastic film body for covering the side of the second space of the communication hole so as to prevent a reverse flow of the fluid, and another elastic film body for covering the side of the another second space of the another communication hole so as to prevent a reverse flow of the fluid, are also provided. An elastic member having a wall portion surrounding the communication hole and another wall portion surrounding the another communication hole for holding the elastic film body and the another elastic film body are also provided. A nipping member for nipping the elastic member with the partition wall is also provided. A surface of the elastic member is closely attached to a surface on the side of the second space of the partition wall, a back surface on the opposite side of the surface is closely attached to the nipping member. The nipping member has a protruding portion protruding on the side of the partition wall. The protruding portion is fitted into a space surrounded by the wall portion so as to be in surface contact with the entire circumference of the wall portion to restrict positional displacement of the wall portion, so that deformation due to distortion of the elastic film body is suppressed. The protruding portion is fitted into another space surrounded by the another wall portion so as to be in surface contact with the entire circumference of the another wall portion to restrict positional displacement of the another wall portion, so that deformation due to distortion of the another elastic film body is suppressed. The elastic film body, the another elastic film body, and the elastic member are integrated.

In a check valve structure according to one or more embodiments of the present invention, the elastic member is formed so that the wall portion has larger thickness than thickness of the elastic film body.

A check valve structure according to one or more embodiments of the present invention further includes a nipping member for nipping the elastic member with the partition wall. A surface of the elastic member is closely attached to a surface on the side of the second space of the partition wall, and a back surface on the opposite side of the surface is closely attached to the nipping member. The nipping member has a protruding portion protruding on the side of the partition wall. The protruding portion is fitted into a space surrounded by the wall portion so as to suppress the deformation due to the distortion of the elastic film body.

In one or more embodiments of the present invention, the protruding portion and the wall portion are formed so as to have a size relationship in which the protruding portion is pressed and fitted into the space surrounded by the wall portion.

In one or more embodiments of the present invention, a surface facing the wall portion is chamfered in a protruding end of the protruding portion.

A diaphragm pump according to one or more embodiments of the present invention is a pump for transporting gas by a capacity change of a pump chamber. The diaphragm pump includes a suction valve for bringing the gas into the pump chamber, and a discharge valve for bringing the gas out of the pump chamber. Any of the above check valve structures is used for at least one of the suction valve and the discharge valve.

A sphygmomanometer according to one or more embodiments of the present invention includes a cuff attached to a blood pressure measuring site of a person to be measured, the cuff having a gas bag to be charged with gas. The above diaphragm pump for transferring the gas to the gas bag is also provided. A pressure detector for detecting pressure in the cuff is also provided. A measuring unit for measuring blood pressure of the person to be measured from a pressure value detected by the pressure detector is also provided.

According to the check valve structure of one or more embodiments of the present invention, the deformation due to the distortion of the elastic film body for preventing the reverse flow of the fluid is suppressed. In other words, the check valve is formed so that a shape of the valve is not easily deformed due to the distortion. Therefore, the shape of the valve can be held even in time of assembling and actuating the pump, so that the deformation due to the distortion of the thin-film shape check valve can be suppressed. Therefore, the close attachment states between the valve and the air hole are not easily changed, so that the decrease in the pump efficiency due to the air leakage can be suppressed. Thus, a pump operation can be stably performed.

DETAILED DESCRIPTION

Figure 1:
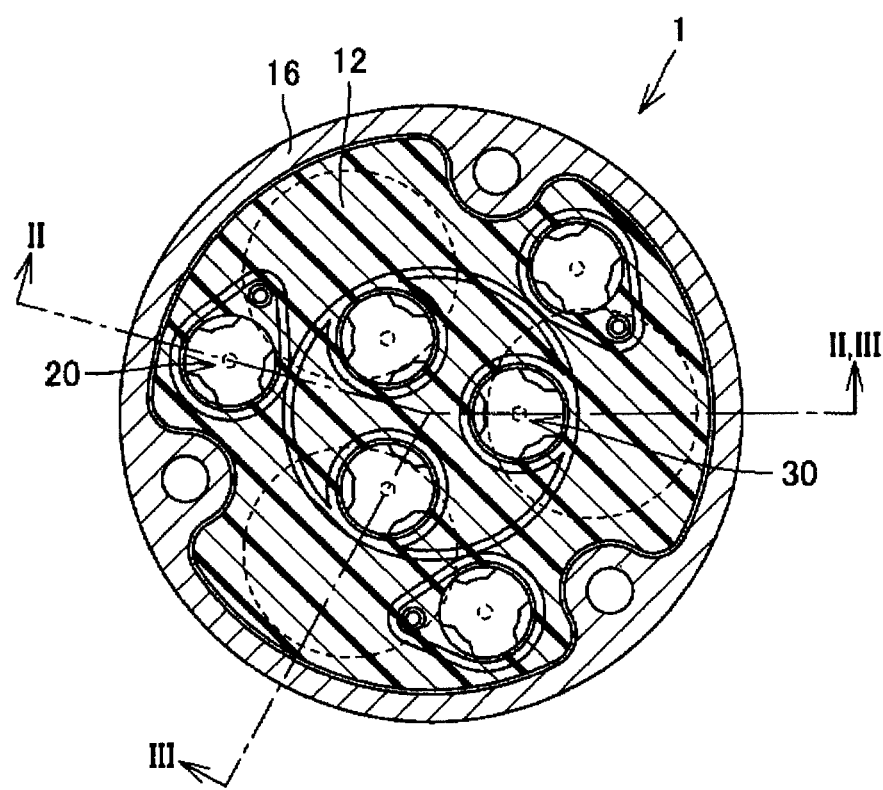
FIG. 1 is a schematic plan view showing a configuration of a diaphragm pump provided with a check valve structure according to one or more embodiments of the present invention.

Embodiments of this invention will be hereinafter described with reference to the drawings. It should be noted that in the following figures, the same reference numerals are given to the same or corresponding parts, and the description thereof will not be repeated.

It should be noted that in the embodiment described below, constituent elements are not always essential to the present invention unless specifically described as being essential. In the following embodiment, in a case where the number, an amount, and the like are referred to, the number, and the like are only examples unless specifically described. Thus, the scope of the present invention is not always limited to the number, the amount, and the like.

Figure 2:
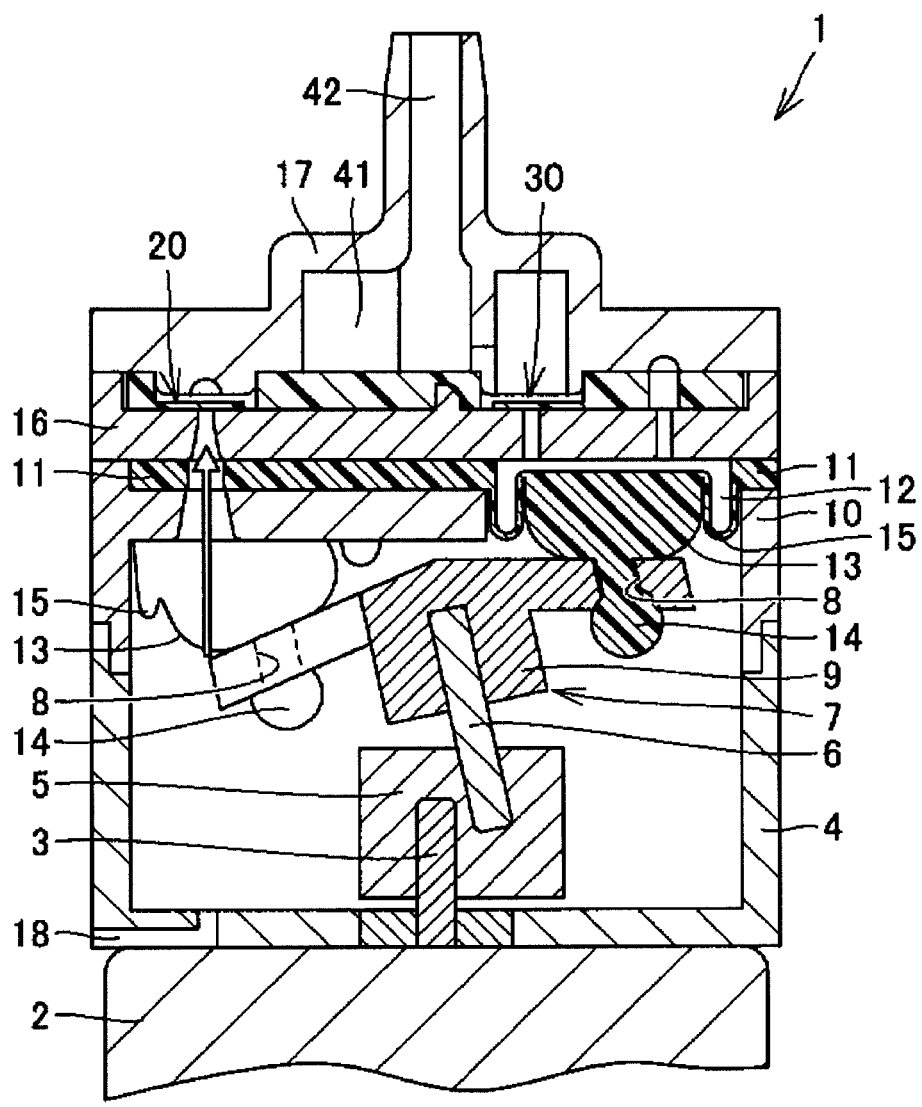
FIG. 2 is a schematic sectional view along the line II-II shown in FIG. 1.
Figure 3:
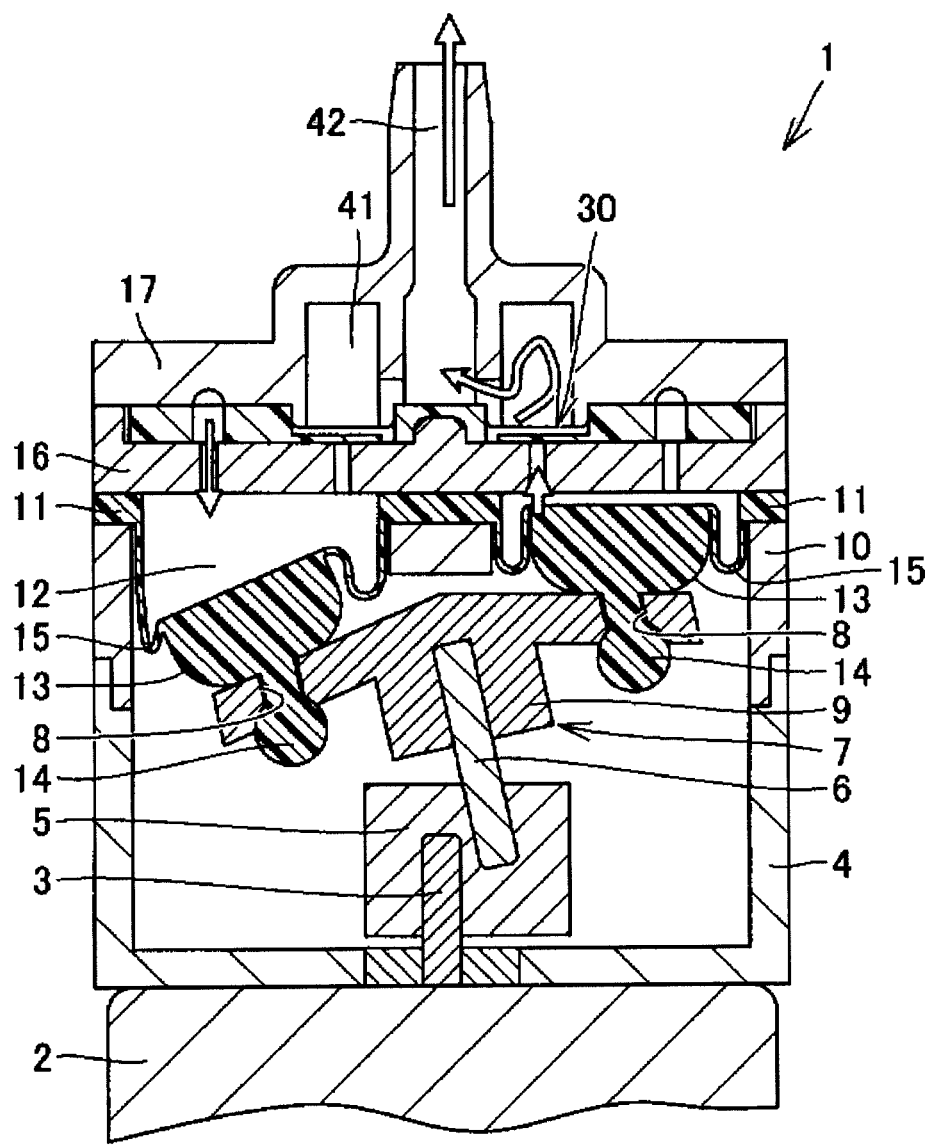
FIG. 3 is a schematic sectional view along the line III-III shown in FIG. 1.

FIG. 1 is a schematic plan view showing a configuration of a diaphragm pump provided with a check valve structure according to one or more embodiments of the present invention. FIG. 2 is a schematic sectional view along the line II-II shown in FIG. 1. FIG. 3 is a schematic sectional view along the line III-III shown in FIG. 1. As shown in FIGS. 1 to 3, a motor 2 serving as a small DC motor is provided in a lower part of a diaphragm pump 1. An output shaft 3 rotated by a rotation motion of the motor 2 is attached to the motor 2. The output shaft 3 extends up to the inside of a lower case 4 of a diaphragm pump 1.

A collar 5 is fixed to an end of the output shaft 3. The collar 5 performs the rotational motion integrally with the output shaft 3. A drive shaft 6 is fixed to the collar 5. A base end serving as one end of the drive shaft 6 fixed to the collar 5 is positioned to be distant from an extension line of a rotation center of the output shaft 3. Meanwhile, an extension line of a center axis in the other end of the drive shaft 6 crosses the extension line of the rotation center of the output shaft 3. Therefore, the drive shaft 6 is inclined relative to the output shaft 3.

The distal end of the drive shaft 6 is rotatably inserted into a drive body 7. The drive body 7 in a plan view is formed into a circular shape. In the drive body 7, three through holes 8 are formed so as to be spaced from each other at 120° intervals. In a lower part of the drive body 7, a tubular support portion 9 extending in the direction in which the drive shaft 6 extends is formed, and the distal end of the drive shaft 6 is rotatably inserted into a hole provided in a center of the support portion 9. An upper case 10 is arranged so as to surround a periphery of the drive body 7. A lower end of the upper case 10 is fixed to an upper end of the lower case 4 by a screw operation or the like.

A diaphragm main body 11 is provided on the upper side of the upper case 10. The diaphragm main body 11 is made of an elastic material such as soft and thin rubber or the like, and formed into a disc shape. In a lower part of the diaphragm main body 11, bell shape pump chambers 12 are formed so as to be equally spaced from each other at 120° intervals. Each of the pump chambers 12 is surrounded by an extendable and contractible diaphragm portion 15, and a drive unit 13 for extending and contracting the diaphragm portion 15 so as to increase and decrease a capacity of the pump chamber 12.

The drive unit 13 is provided on the lower side of the pump chamber 12. A head portion 14 is formed in a distal end of the drive unit 13 through a thin neck portion. The head portion 14 passing through the through hole 8 formed in the drive body 7 is arranged so that the neck portion is positioned inside the through hole 8. Thus, the diaphragm main body 11 is assembled to the drive body 7.

A valve housing 16 is provided on the upper side of the diaphragm main body 11. An air collection body 17 is provided on the further upper side of the valve housing 16. Suction valves 20 and discharge valves 30 are arranged so as to be nipped between the valve housing 16 and the air collection body 17. Gas to be transported by this diaphragm pump 1 flows from an air chamber 41 formed inside the air collection body 17, an exhaust portion 42, to an exterior. It should be noted that schematic plan views in FIGS. 1, 4 and 6 described later show plan views of the diaphragm pump 1 in a section in which the suction valves 20 and the discharge valves 30 are provided.

Figure 4:
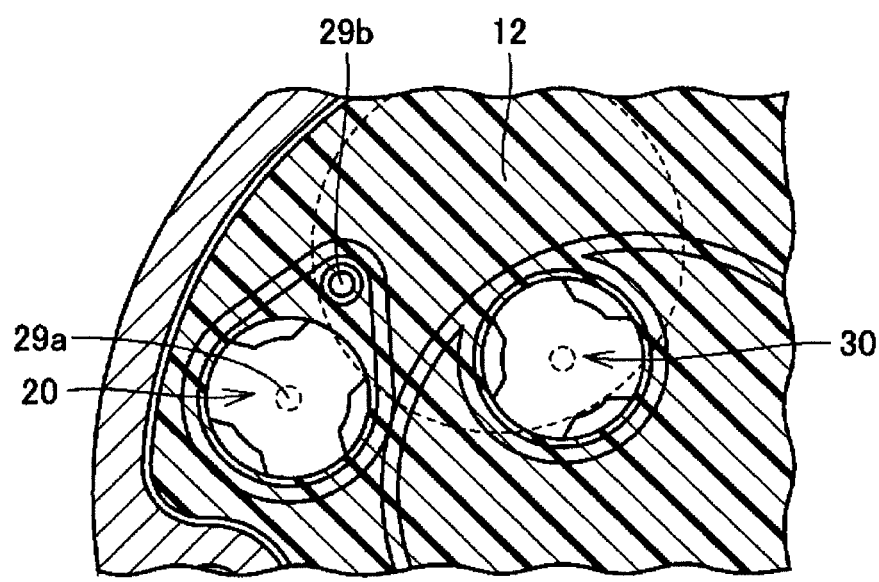
FIG. 4 is an enlarged schematic plan view of the diaphragm pump showing a suction valve and a periphery thereof.
Figure 5:
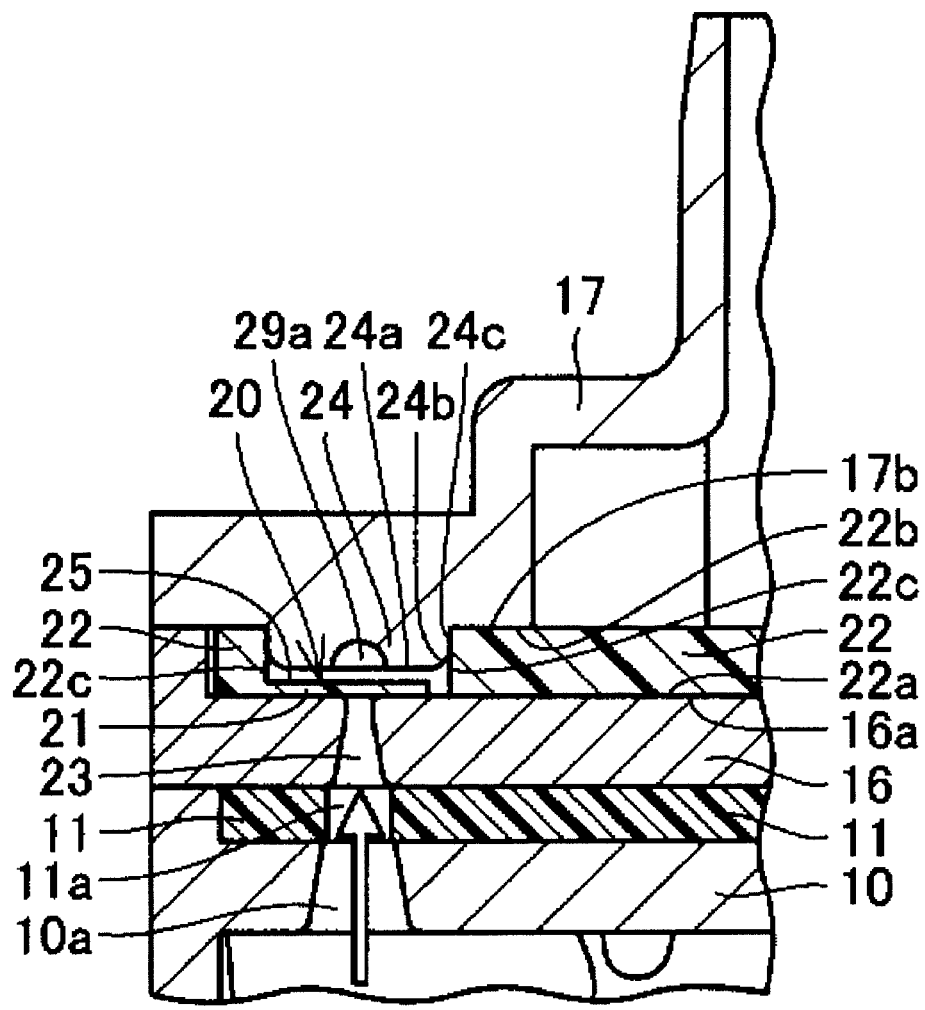
FIG. 5 is an enlarged schematic sectional view of the diaphragm pump showing the suction valve and the periphery thereof.

The check valve structure will be hereinafter described. FIG. 4 is an enlarged schematic plan view of the diaphragm pump showing the suction valve and a periphery thereof. FIG. 5 is an enlarged schematic sectional view of the diaphragm pump showing the suction valve and the periphery thereof. With reference to FIGS. 4 and 5, each of the suction valves 20 for bringing the gas into the pump chamber 12 includes an elastic film body 21, and an elastic member 22 formed so as to surround the elastic film body 21 for holding the elastic film body 21. The elastic member 22 has a wall portion 22c, and the elastic film body 21 is provided in a space 25 surrounded by the wall portion 22c.

A surface 22a of the elastic member 22 is closely attached to a surface 16a on the side of the space 25 of the valve housing 16. A back surface 22b on the opposite side of the surface 22a of the elastic member 22 is closely attached to a surface 17b on the side of the space 25 of the air collection body 17. The elastic member 22 is nipped between the valve housing 16 and the air collection body 17. The air collection body 17 has a function as a nipping member for nipping the elastic member 22 with the valve housing 16.

A space surrounded by the lower case 4, the upper case 10, and the diaphragm main body 11 forms an internal space of the diaphragm pump 1. A suction passage 18 is formed at one point or a plurality of points in at least one of the lower case 4 and the upper case 10, so as to provide communication between the internal space of the diaphragm pump 1 and the exterior of the diaphragm pump 1. The air from an exterior of the system flows into the internal space of the diaphragm pump 1 via the suction passage 18.

As shown in FIG. 5, the internal space of the diaphragm pump 1 and the space 25 surrounded by the wall portion 22c are partitioned by the upper case 10, the diaphragm main body 11, and the valve housing 16. Communication holes 10a, 11a, 23 providing communication between the internal space of the diaphragm pump 1 and the space 25 are respectively formed in the upper case 10, the diaphragm main body 11, and the valve housing 16.

The valve housing 16 is included in a partition wall for partitioning the internal space of the diaphragm pump 1 serving as a first space and the space 25 serving as a second space. The valve housing 16 is arranged between the internal space of the diaphragm pump 1 and the space 25. A communication hole 23 providing communication between the internal space of the diaphragm pump 1 and the space 25 is formed in the valve housing 16. The elastic film body 21 covers the communication hole 23 formed in the valve housing 16 from the side of the space 25. The wall portion 22c of the elastic member 22 is formed so as to surround the communication hole 23.

The air collection body 17 serving as the nipping member for nipping the elastic member 22 with the valve housing 16 has a protruding portion 24 formed by protruding part of the air collection body 17 on the side of the valve housing 16. The protruding portion 24 protrudes toward the inside of the space 25 surrounded by the wall portion 22c of the elastic member 22. The protruding portion 24 is pressed and fitted into the space 25 on the upper side of the elastic film body 21. A side wall 24c of the protruding portion 24 is in contact with the wall portion 22c of the elastic member 22. The protruding portion 24 is formed by protruding the air collection body 17 serving as a member facing the valve housing 16 in contact with the elastic film body 21 through the space 25 toward the inside of the space 25. The protruding portion 24 is formed by protruding the air collection body 17 serving as one of the members for nipping the elastic member 22 on the side of the valve housing 16 serving as the other member.

A chamfered portion 24b is formed in a peripheral edge of a protruding end 24a serving as a distal end of the protruding portion 24 projecting in the space 25. The chamfered portion 24b is formed in a distal end of the side wall 24c in contact with the wall portion 22c of the elastic member 22. The side wall 24c serving as a side surface facing the wall portion 22c of the elastic member 22 is chamfered, so that the chamfered portion 24b is formed in the protruding end 24a of the protruding portion 24.

The elastic member 22 is formed so that the wall portion 22c has larger thickness than thickness of the elastic film body 21. For example, the elastic film body 21 and the elastic member 22 can be formed so that the thickness of the wall portion 22c of the elastic member 22 is about five times more than the thickness of the elastic film body 21. For example, the thickness of the elastic film body 21 can be 0.3 mm, and the thickness of the elastic member 22 can be 1.5 mm.

A ventilation passage 29a is formed inside the protruding portion 24. The ventilation passage 29a communicates with a ventilation passage 29b shown in FIG. 4 via a ventilation passage (not shown) formed inside the air collection body 17. The space 25 and the pump chamber 12 communicate with each other via the ventilation passages 29a, 29b formed in the air collection body 17, and a ventilation hole 29c formed in an elastic member 32 and ventilation hole 29d formed in the valve housing 16 both described later and shown in FIG. 7.

Figure 6:
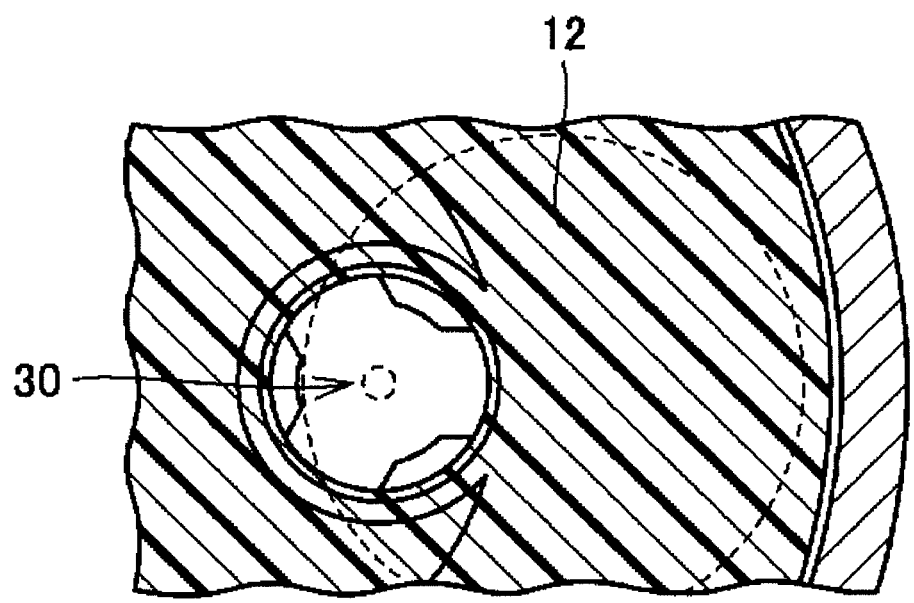
FIG. 6 is an enlarged schematic plan view of the diaphragm pump showing a discharge valve and a periphery thereof.
Figure 7:
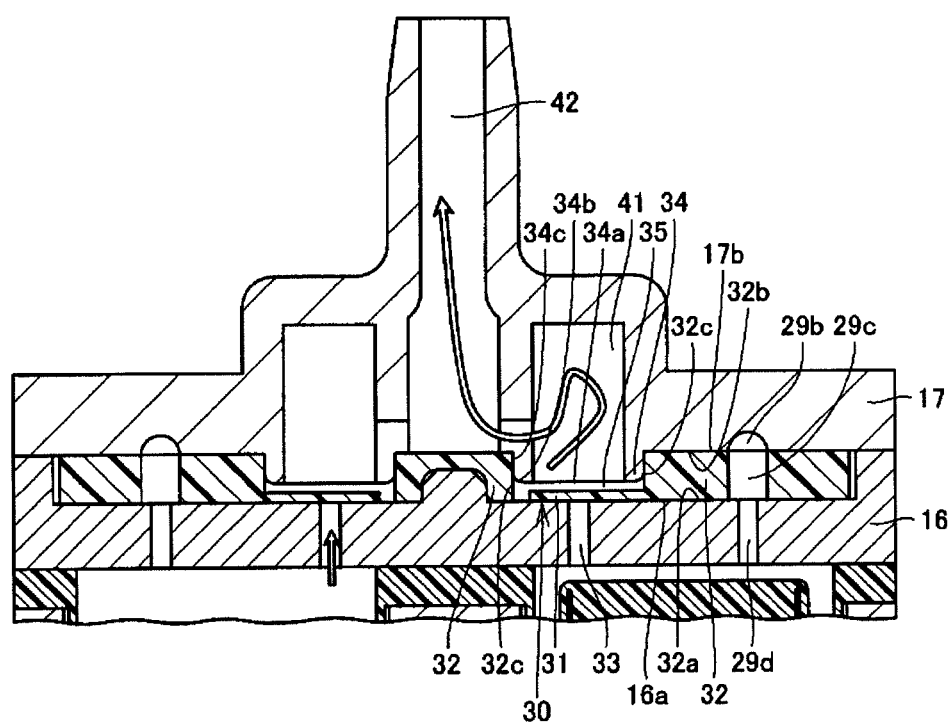
FIG. 7 is an enlarged schematic sectional view of the diaphragm pump showing the discharge valve and the periphery thereof.

FIG. 6 is an enlarged schematic plan view of the diaphragm pump showing the discharge valve and a periphery thereof. FIG. 7 is an enlarged schematic sectional view of the diaphragm pump showing the discharge valve and the periphery thereof. With reference to FIGS. 6 and 7, each of the discharge valves 30 for bringing the gas out of the pump chamber 12 includes an elastic film body 31, and the elastic member 32 formed so as to surround the elastic film body 31 for holding the elastic film body 31. The elastic member 32 has a wall portion 32c, and the elastic film body 31 is provided in a space 35 surrounded by the wall portion 32c.

A surface 32a of the elastic member 32 is closely attached to the surface 16a on the side of the space 35 of the valve housing 16. A back surface 32b on the opposite side of the surface 32a of the elastic member 32 is closely attached to the surface 17b on the side of the space 35 of the air collection body 17. The elastic member 32 is nipped between the valve housing 16 and the air collection body 17. The air collection body 17 has a function as a nipping member for nipping the elastic member 32 with the valve housing 16.

As shown in FIG. 7, the pump chamber 12 and the space 35 surrounded by the wall portion 32c are partitioned by the valve housing 16. A communication hole 33 providing communication between the pump chamber 12 and the space 35 is formed in the valve housing 16. The valve housing 16 is a partition wall for partitioning the pump chamber 12 serving as the first space and the space 35 serving as the second space. The valve housing 16 is arranged between the pump chamber 12 and the space 35. The elastic film body 31 covers the communication hole 33 formed in the valve housing 16 from the side of the space 35. The wall portion 32c of the elastic member 32 is formed so as to surround the communication hole 33.

The air collection body 17 serving as the nipping member for nipping the elastic member 32 with the valve housing 16 has a protruding portion 34 formed by protruding part of the air collection body 17 on the side of the valve housing 16. The protruding portion 34 protrudes toward the inside of the space 35 surrounded by the wall portion 32c of the elastic member 32. The protruding portion 34 is pressed and fitted into the space 35 on the upper side of the elastic film body 31. A side wall 34c of the protruding portion 34 is in contact with the wall portion 32c of the elastic member 32. The protruding portion 34 is formed by protruding the air collection body 17 serving as a member facing the valve housing 16 in contact with the elastic film body 31 through the space 35 toward the inside of the space 35. The protruding portion 34 is formed by protruding the air collection body 17 serving as one of the members for nipping the elastic member 32 on the side of the valve housing 16 serving as the other member.

A chamfered portion 34b is formed in a peripheral edge of a protruding end 34a serving as a distal end of the protruding portion 34 projecting in the space 35. The chamfered portion 34b is formed in a distal end of the side wall 34c in contact with the wall portion 32c of the elastic member 32. The side wall 34c serving as a side surface facing the wall portion 32c of the elastic member 32 is chamfered, so that the chamfered portion 34b is formed in the protruding end 34a of the protruding portion 34.

The elastic member 32 is formed so that the wall portion 32c has larger thickness than thickness of the elastic film body 31. For example, the elastic film body 31 and the elastic member 32 can be formed so that the thickness of the wall portion 32c of the elastic member 32 is about five times more than the thickness of the elastic film body 31. For example, the thickness of the elastic film body 31 can be 0.3 mm, and the thickness of the elastic member 32 can be 1.5 mm.

An operation of the diaphragm pump 1 of the present embodiment will be hereinafter described. When electric power is applied to the motor 2 and the output shaft 3 is rotated, the drive shaft 6 serving as an inclination shaft is rotated. The drive body 7 is assembled to the drive shaft 6, and also assembled to the head portion 14 of the drive unit 13 in each of the pump chamber 12. Therefore, by the rotation of the drive shaft 6, an assembled part of the drive body 7 and the head portion 14 of the drive unit 13 in the pump chamber 12 is oscillated in the up and down direction with a phase difference of 120°. The diaphragm portion 15 is extended and contracted by the oscillation in the up and down direction of this drive unit 13, so as to periodically change the capacity of the pump chamber 12. That is, when the drive unit 13 is moved downward, the capacity of the pump chamber 12 is increased. When the drive unit 13 is moved upward, the capacity of the pump chamber 12 is decreased.

Figure 8:
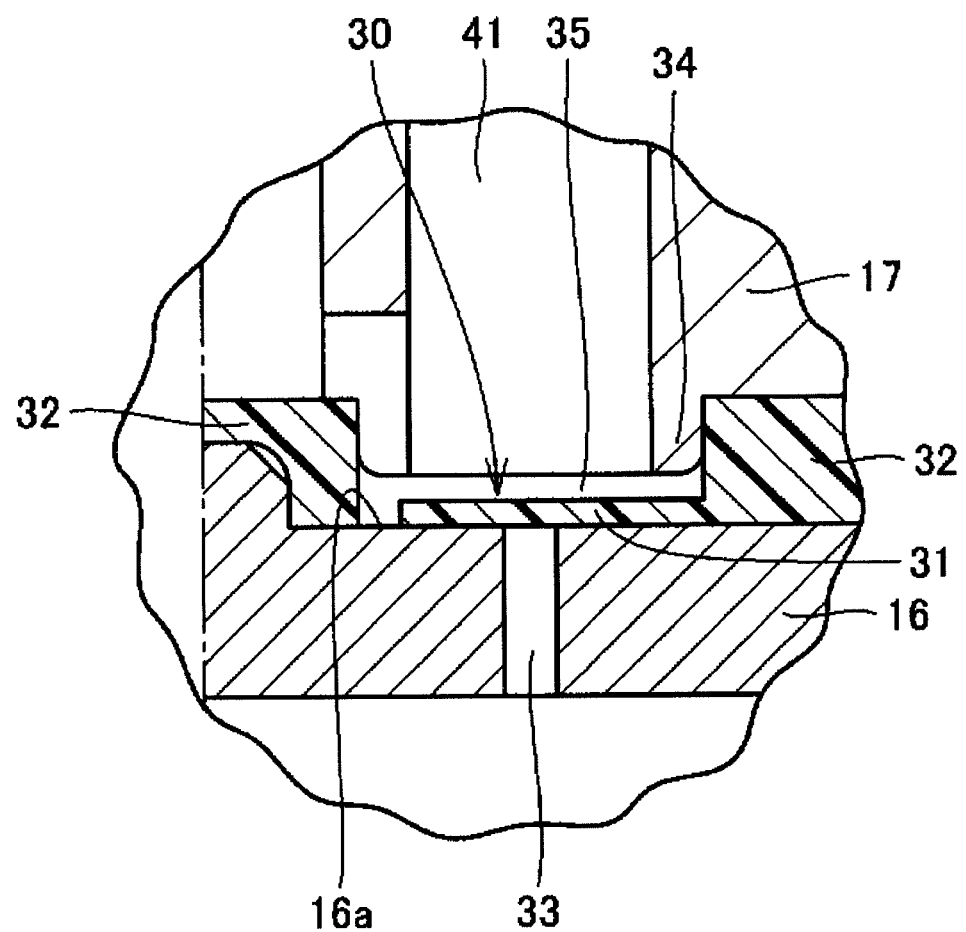
FIG. 8 is an enlarged schematic sectional view showing a state that an elastic film body is closed.

When the drive unit 13 is moved downward and the capacity of the pump chamber 12 is increased, the inside of the pump chamber 12 is depressurized. When the inside of the pump chamber 12 is depressurized, as shown in FIG. 8, the elastic film body 31 serving as a valve body of the discharge valve 30 is closely attached to the surface 16a of the valve housing 16, so that the discharge valve 30 is closed. Meanwhile, the elastic film body 21 serving as a valve body of the suction valve 20 is elastically deformed by a change in pressure inside the pump chamber 12 so as to be moved inside the space 25. Thereby, the suction valve 20 is opened, so that the air flows into the pump chamber 12 via the suction valve 20.

Figure 9:
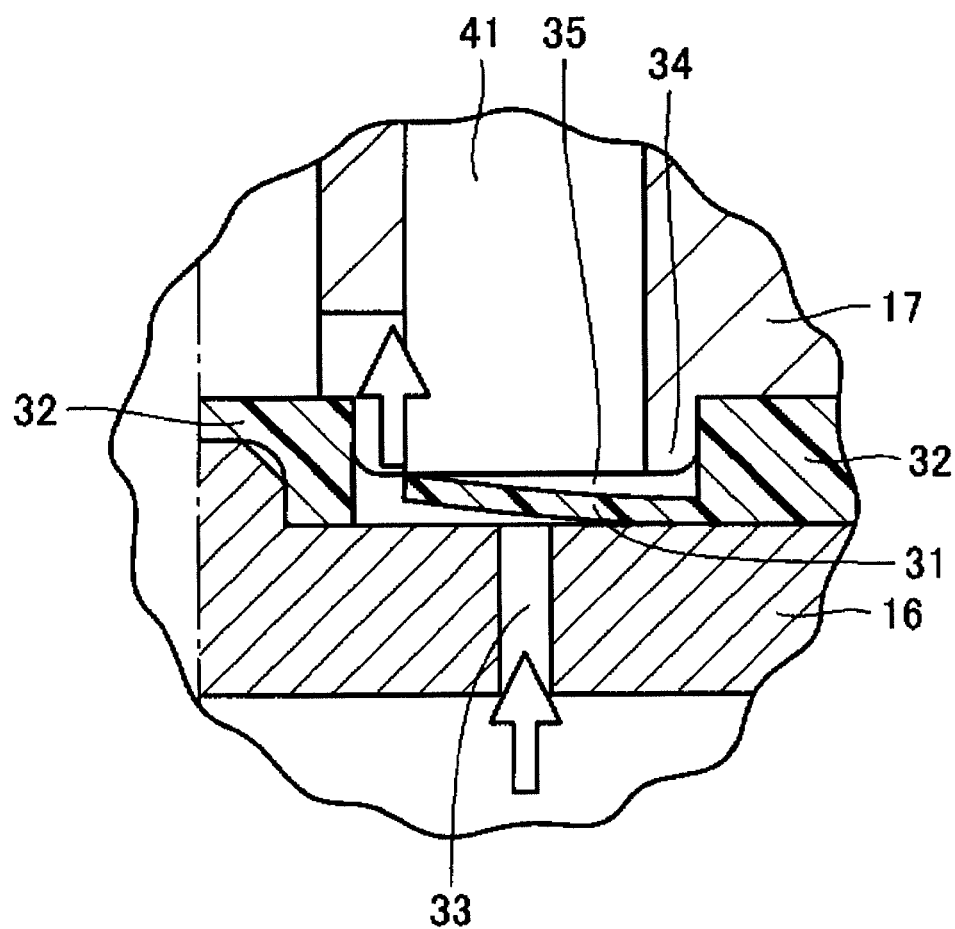
FIG. 9 is an enlarged schematic sectional view showing a state that the elastic film body is opened.

When the drive unit 13 is moved upward and the capacity of the pump chamber 12 is decreased, the pressure inside the pump chamber 12 is intensified. When the pressure inside the pump chamber 12 is intensified, the elastic film body 21 of the suction valve 20 is closely attached to the surface 16a of the valve housing 16, so that the suction valve 20 is closed. Meanwhile, as shown in FIG. 9, the elastic film body 31 of the discharge valve 30 is elastically deformed by the change in the pressure inside the pump chamber 12 so as to be moved inside the space 35. Thereby, the discharge valve 30 is opened, so that the air flows out of the pump chamber 12 via the discharge valve 30. It should be noted that FIG. 8 is an enlarged schematic sectional view showing a state that the elastic film body is closed. FIG. 9 is an enlarged schematic sectional view showing a state that the elastic film body is opened.

By the change in the capacity of the pump chamber 12 as described above, the diaphragm pump 1 transports the gas.

The air flowing out of the pump chamber 12 via the discharge valve 30 flows from the air chamber 41 formed inside the air collection body 17, the exhaust portion 42, to the exterior. The suction valve 20 works as a check valve for allowing a flow of the gas from the internal space of the diaphragm pump 1 to the pump chamber 12 and inhibiting a flow in the reverse direction thereof. The discharge valve 30 works as a check valve for allowing a flow of the gas from the pump chamber 12 to the exhaust portion 42 and inhibiting a flow in the reverse direction thereof.

The three pump chambers 12 are formed in the diaphragm pump 1 of the present embodiment. Each of the pump chambers 12 performs one pump operation for one rotation of the drive body 7. For the entire diaphragm pump 1, three pump operations are successively performed with a fixed phase difference, so that pulsation of the air flow is reduced and operation efficiency is favorable. The pump chambers 12 are formed integrally with the motor 2, a plurality of the pump chambers 12 is arranged in a periphery of the output shaft 3 taking the rotation center of the output shaft 3 as an axis, and further the drive body 7 is arranged between the motor 2 and the pump chambers 12. Therefore, the pump devices and the motor 2 are integrated, so that a shape of the diaphragm pump 1 is highly small.

When the diaphragm pump 1 is small in size as described above, distortion is easily generated in shapes of the thin-film shape check valves (that is, the elastic film bodies 21, 31) in time of assembling and actuating the diaphragm pump 1. When the distortion is generated in the shapes of the elastic film bodies 21, 31, close attachment states between the elastic film bodies 21, 31 and the valve housing 16 are changed, so that air leakage is generated. Thus, pump efficiency is decreased in time of actuating the pump.

Therefore, in the check valve structure of the present embodiment, the protruding portions 24, 34 are formed in the air collection body 17 as deformation suppressing portions for suppressing deformation due to the distortion of the elastic film bodies 21, 31. Since the protruding portions 24, 34 are respectively fitted into the spaces 25, 35, positional displacement of the wall portions 22c, 32c formed so as to surround the communication holes 23, 33 and the elastic film bodies 21, 31 is restricted, so that the distortion of the shapes of the elastic members 22, 32 is suppressed. As a result, the deformation due to the distortion of the elastic film bodies 21, 31 can be suppressed, so that a decrease in the efficiency of the diaphragm pump 1 due to the air leakage can be suppressed.

Figure 10:
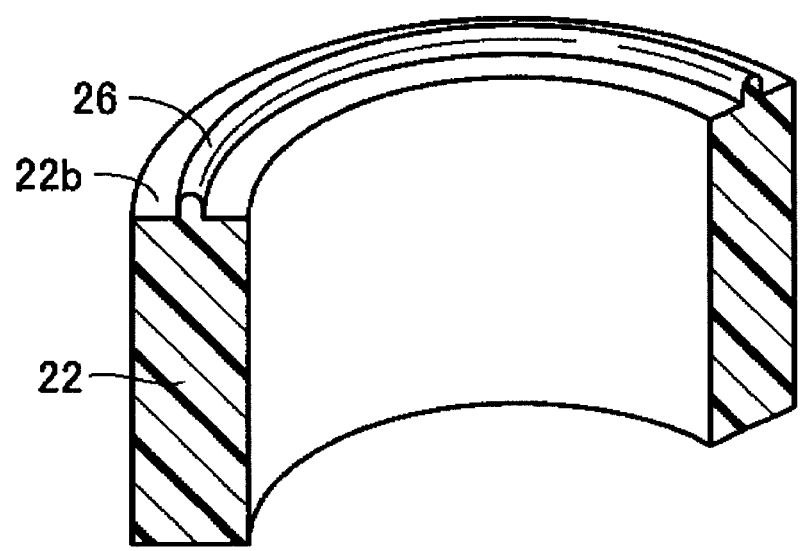
FIG. 10 is a schematic sectional view partially showing a shape of an elastic member.

FIG. 10 is a schematic sectional view partially showing a shape of the elastic member. As shown in FIG. 10, a bead 26 serving as a liner protrusion is formed on the back surface 22b serving as a surface of the elastic member 22 closely attached to the air collection body 17. As nipped between the valve housing 16 and the air collection body 17 in an assembling process of the diaphragm pump 1, the bead 26 is squeezed so as to be closely attached to the air collection body 17. Thus, the air leakage from a gap between the elastic member 22 and the air collection body 17 can be suppressed. Since the air leakage can be easily suppressed by the formation of bead 26, assembling precision of the diaphragm pump 1 can be improved.

The elastic film bodies 21, 31 and the elastic members 22, 32 can be made of an elastic material such as rubber. For example, NBR (nitrile rubber), CR (chloroprene rubber), EPDM (ethylene-propylene rubber), TPE (thermoplastic elastomer), and the like can be used as the elastic material. The valve housing 16 and the air collection body 17 to which the elastic members 22, 32 are closely attached can be made of a resin material. For example, ABS (acrylonitrile butadiene styrene resin), PS (polystyrene resin), POM (polyoxymethylene resin), and the like can be used as the resin material.

As described above, the suction valve 20 of the present embodiment has the check valve structure for allowing the flow of the gas from the internal space of the diaphragm pump 1 to the pump chamber 12 and inhibiting the flow in the reverse direction thereof. The suction valve 20 includes the valve housing 16 arranged between the internal space of the diaphragm pump 1 and the space 25 and provided with the communication hole 23 providing communication between the internal space of the diaphragm pump 1 and the space 25. The suction valve 20 also includes the elastic film body 21 for covering the side of the space 25 of the communication hole 23 so as to prevent a reverse flow of the gas. The suction valve 20 also includes the elastic member 22 having the wall portion 22c surrounding the communication hole 23 for holding the elastic film body 21. The suction valve 20 further includes the air collection body 17 for nipping the elastic member 22 with the valve housing 16.

The surface 22a of the elastic member 22 is closely attached to the surface 16a on the side of the space 25 of the valve housing 16, and the back surface 22b on the opposite side of the surface 22a is closely attached to the air collection body 17. The air collection body 17 has the protruding portion 24 formed by protruding the air collection body 17 on the side of the valve housing 16. Since the protruding portion 24 is fitted into the space 25 surrounded by the wall portion 22c so as to restrict the positional displacement of the wall portion 22c, the deformation due to the distortion of the elastic film body 21 is suppressed.

Meanwhile, the discharge valve 30 of the present embodiment has the check valve structure for allowing the flow of the gas from the pump chamber 12 to the exhaust portion 42 and inhibiting the flow in the reverse direction thereof. The discharge valve 30 includes the valve housing 16 arranged between the pump chamber 12 and the space 35 and provided with the communication hole 33 providing communication between the pump chamber 12 and the space 35. The discharge valve 30 also includes the elastic film body 31 for covering the side of the space 35 of the communication hole 33 so as to prevent a reverse flow of the gas. The discharge valve 30 also includes the elastic member 32 having the wall portion 32c surrounding the communication hole 33 for holding the elastic film body 31. The discharge valve 30 further includes the air collection body 17 for nipping the elastic member 32 with the valve housing 16.

The surface 32a of the elastic member 32 is closely attached to the surface 16a on the side of the space 35 of the valve housing 16, and the back surface 32b on the opposite side of the surface 32a is closely attached to the air collection body 17. The air collection body 17 has the protruding portion 34 formed by protruding the air collection body 17 on the side of the valve housing 16. Since the protruding portion 34 is fitted into the space 35 surrounded by the wall portion 32c so as to restrict the positional displacement of the wall portion 32c, the deformation due to the distortion of the elastic film body 31 is suppressed.

Accordingly, since the protruding portions 24, 34 are respectively fitted into the spaces 25, 35, the positional displacement that the wall portions 22c, 32c of the elastic members 22, 32 formed so as to surround the communication holes 23, 33 and the elastic film bodies 21, 31 are moved relative to the valve housing 16 due to the deformation or the like in time of forming, transporting or assembling can be restricted. Thus, the distortion of the shapes of the elastic members 22, 32 is suppressed. Therefore, the deformation due to the distortion of the elastic film bodies 21, 31 preventing the reverse flow of the gas is suppressed. As a result, the shapes of the suction valve 20 and the discharge valve 30 can be held even in time of assembling and actuating the diaphragm pump 1, so that the deformation of the elastic film bodies 21, 31 serving as soft and easily-deformable rubber thin films can be suppressed. In other words, the suction valve 20 and the discharge valve 30 are formed so that the shapes of the valves are not easily deformed. Therefore, the close attachment states of the elastic film bodies 21, 31 to the valve housing 16 provided with the communication holes 23, 33 through which the air flows are not easily changed.

The spaces 25, 35 can be formed into a cylindrical shape having the peripheral wall portions 22c, 32c formed into a circular shape in a plan view. Accordingly, when shapes of the protruding portions 24, 34 corresponding to the wall portions 22c, 32c are formed into a cylindrical shape and fitted to the wall portions, the air leakage from the elastic members 22, 32 in peripheries of the elastic film bodies 21, 31 can be prevented. It should be noted that in the above structure, when the protruding portions 24, 34 and the wall portions 22c, 32c are formed so as to have a size relationship in which the protrusion portions 24, 34 are pressed and fitted into the spaces 25, 35, an air leakage preventing effect is more improved. By adopting the above structure, the air leakage from the spaces 25, surrounded by the wall portions 22c, 32c can be prevented. Thus, the bead 26 shown in FIG. 10 can be eliminated.

The protruding portions 24, 34 are formed in the air collection body 17 for nipping the elastic members 22, 32 with the valve housing 16. Therefore, the protruding portions 24, 34 can be fitted into the spaces 25, 35 in time of attaching the air collection body 17 to the valve housing 16. Thus, a process for attaching the protruding portions 24, 34 is not particularly required. In a case where the air collection body 17 is made of the resin material, the protruding portions 24, 34 can be integrally formed. Therefore, productivity of the diaphragm pump 1 can be improved, and an effect of reducing manufacturing cost can also be obtained.

The suction valve 20 having the elastic film body 21 and the discharge valve 30 having the elastic film body 31 can be integrally formed. For example, the elastic member 22 and the elastic member 32 are integrally formed by a sheet shape elastic material, and part of the sheet shape elastic material is thinned so as to form an elastic film body 21, 31. Accordingly, one integrated valve body can be used for a plurality of the diaphragms. Thus, reduction in the number of parts, reduction in assembling manhour, and cost reduction can be achieved.

The suction valve 20 and the discharge valve 30 can be formed into the same shape. With this configuration, productivity of the valve bodies can be improved. Thus, more cost reduction can be achieved.

In the suction valve 20, the elastic member 22 is formed so that the wall portion 22c has larger thickness than the thickness of the elastic film body 21. Similarly, in the discharge valve 30, the elastic member 32 is formed so that the wall portion 32c has larger thickness than the thickness of the elastic film body 31. With this configuration, strength of the elastic members 22, 32 can be improved. Thus, even when the protruding portions 24, 34 are pressed into the spaces 25, formed in the elastic members 22, 32, the deformation of the elastic members 22, 32 can be suppressed.

The side walls 24c, 34c of the protruding portions 24, 34 can be in contact with the wall portions 22c, 32c. That is, the elastic members 22, 32 and the protruding portions 24, 34 can be in surface contact with each other. Thus, the air leakage from the gaps between the elastic members 22, 32 and the protruding portions 24, 34 can be more suppressed. When the protruding portions 24, 34 are formed so as to be in surface contact with the entire circumference of the wall portions 22c, 32c forming side surfaces of the spaces 25, 35, the air leakage of the check valves can be further suppressed.

The side walls 24c, 34c serving as the side surfaces facing the wall portions 22c, 32c are chamfered, and the chamfered portions 24b, 34b are formed in the protruding ends 24a, 34a of the protruding portions 24, 34. Accordingly, the protruding portions 24, 34 can be easily inserted and fitted into the spaces 25, 35. Thus, the productivity can be more improved.

In the diaphragm pump 1 of the present embodiment, the check valve structure is used in the suction valve 20 for bringing the gas into the pump chamber 12, and the discharge valve 30 for bringing the gas out of the pump chamber 12. The diaphragm pump 1 transports the gas by the capacity change of the pump chamber 12. As described above, the suction valve 20 and the discharge valve 30 are formed so that the close attachment states between the elastic film bodies 21, 31 and the valve housing 16 are not easily changed. Thus, the decrease in the pump efficiency due to the air leakage in time of actuating the pump can be suppressed. Therefore, an operation of the diaphragm pump 1 can be stably performed.

In the above description, the three pump chambers 12 are provided in the diaphragm pump 1, the three suction valves 20 and the three discharge valves 30 for bringing the gas into and out of the pump chambers 12 are provided as an example. However, the number of the suction valve 20, the discharge valve 30, and the pump chamber 12 is not limited to this. When more pump chambers 12 are provided, a ripple of the pump can be reduced. Thus, noise generated by the pump can be advantageously reduced.

Figure 11:
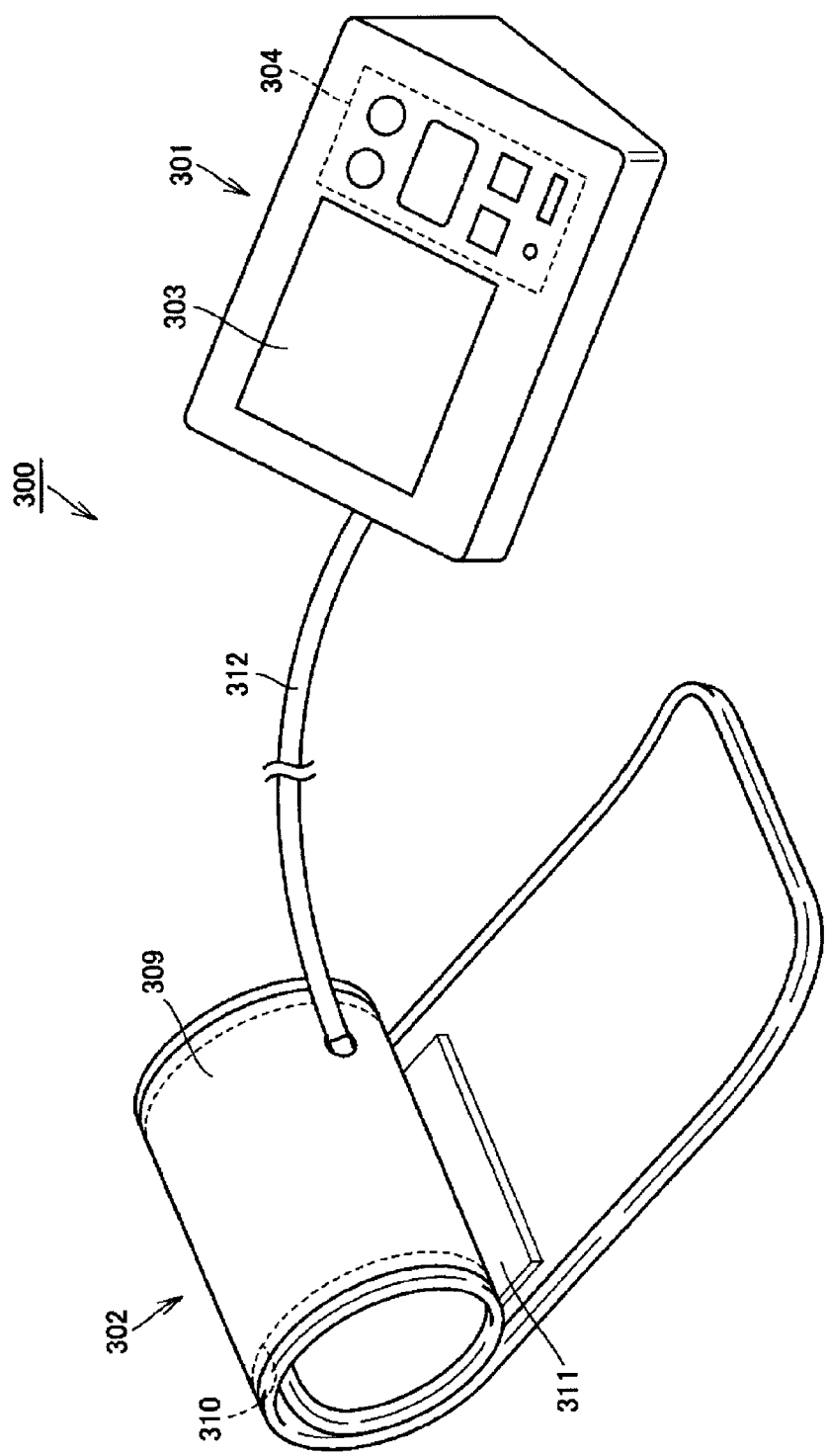
FIG. 11 is an entire perspective view showing an outer appearance of a sphygmomanometer.
Figure 12:
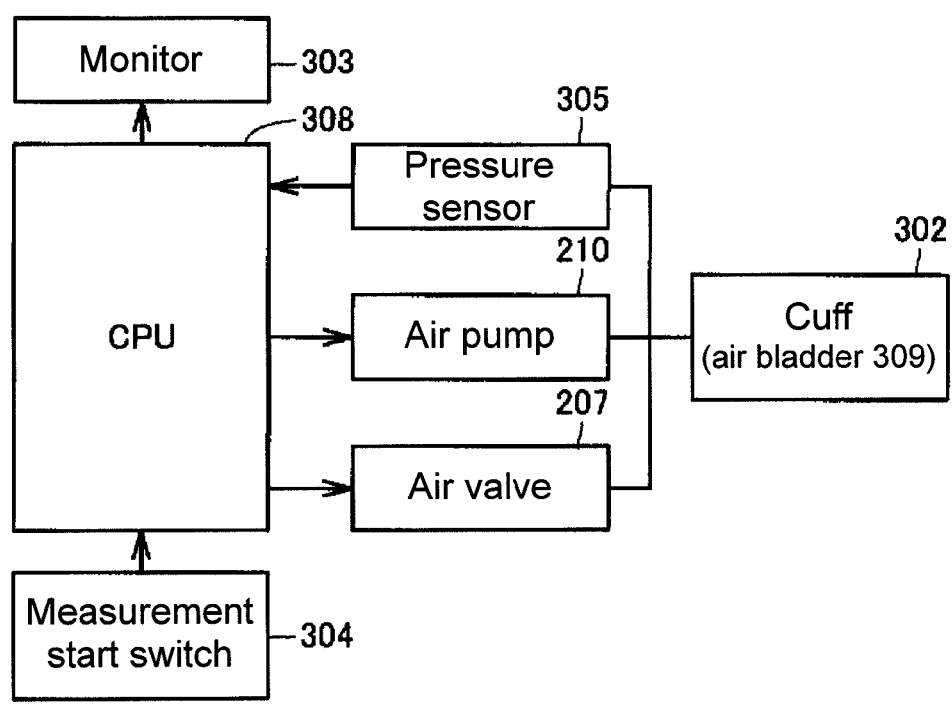
FIG. 12 is a block diagram showing an internal configuration of the sphygmomanometer.

Next, a schematic configuration of a domestic use sphygmomanometer 300 will be described with reference to FIGS. 11 and 12. FIG. 11 is an entire perspective view showing an outer appearance of the sphygmomanometer, and FIG. 12 is a block diagram showing an internal configuration of the sphygmomanometer. With reference to both the figures, the sphygmomanometer 300 includes a main body portion 301 in which a control device of blood pressure measurement is incorporated, a sphygmomanometer cuff 302, and an air tube 312 for coupling the main body portion 301 and the cuff 302.

The cuff 302 has a compressing air bladder 309 in which the air fed from an air pump 210 is charged and stored, the compressing air bladder being used for compressing an artery of a measuring site (an upper arm). The cuff 302 has a strip shape band 310 having the compressing air bladder 309 on the inner surface side thereof to be attached to the measuring site (the upper arm), and a plane fastener 311 for fixing the band 310 wound around the upper arm.

A display unit 303 and an operation unit 304 are provided on an outer surface of the main body portion 301. A pressure sensor 305 serving as a pressure detector for detecting pressure in the cuff 302, the air pump 210 for transferring the gas (the air) to the compressing air bladder 309, and an air valve 207 are provided inside the main body portion 301. A CPU 308 for controlling devices such as the pressure sensor 305, the air pump 210, and the air valve 207 and determining blood pressure of a person to be measured from a pressure value detected by the pressure sensor 205 is provided inside the main body portion 301.

In the sphygmomanometer 300 with the above configuration, in a case where the blood pressure of the person to be measured is measured, the cuff 302 is attached to the blood pressure measuring site (the upper arm) of the person to be measured. When the air valve 207 is closed, all the air discharged from the air pump 210 flows into the compressing air bladder 309, so that the compressing air bladder 309 is pressurized. Meanwhile, when the air valve 207 is opened, the air in the compressing air bladder 309 is released to the exterior via the air valve 207, so that the compressing air bladder 309 is depressurized.

In a case where a small sphygmomanometer pump is used, the air leakage is easily generated from the check valve structure for bringing the gas into and out of the pump chambers. Thus, this sphygmomanometer 300 can include the above diaphragm pump 1 as the air pump 210 for transferring the gas (the air) to the compressing air bladder 309. The diaphragm pump 1 can be stably operated while suppressing the decrease in the pump efficiency due to the air leakage. Thus, the sphygmomanometer 300 provided with the diaphragm pump 1 can be stably operated.

Specific embodiments of the present invention is are described as above. The embodiment disclosed herein is illustrative in all aspects and should not be construed as being restrictive. The scope of the present invention is defined not by the above description but by the claims, and meanings equivalent to the claims and all modifications within the scope are intended to be encompassed herein.

DESCRIPTION OF SYMBOLS

1 Diaphragm pump
2 Motor
3 Output shaft
4 Lower case
5 Collar
6 Drive shaft
7 Drive body
8 Through hole
9 Support portion
10 Upper case
10a, 11a Communication hole
11 Diaphragm main body
12 Pump chamber
13 Drive unit
14 Head portion
15 Diaphragm portion
16 Valve housing
16a Surface
17 Air collection body
17b Surface
18 Suction passage
20 Suction valve
21, 31 Elastic film body
22, 32 Elastic member
22a, 32a Surface
22b, 32b Back surface
22c, 32c Wall portion
23, 33 Communication hole
24, 34 Protruding portion
24a, 34a Protruding end
24b, 34b Chamfered portion
24c, 34c Side wall
25, 35 Space
26 Bead
29a, 29b Ventilation passage
29c, 29d Ventilation hole
30 Discharge valve
41 Air chamber
42 Exhaust portion
300 Sphygmomanometer

The invention claimed is:
1. A check valve structure, comprising:
a first check valve;
a first space and a second space, the first check valve being configured to allow a flow of a fluid from the first space to the second space and inhibit a flow of the fluid from the second space to the first space;
a second check valve;
another first space and another second space, the second check valve being configured to allow a flow of the fluid from the another first space to another second space and inhibit a flow of the fluid from the another second space to the another first space;
a partition wall arranged between the first space and the second space and between the another first space and the another second space and provided with a communication hole providing communication between the first space and the second space and another communication hole providing communication between the another first space and the another second space;
the first check valve comprising a first elastic film body that covers and directly contacts a side of the second space of the communication hole so as to prevent a reverse flow of the fluid when the first elastic film body is in a first closed position;
the second check valve comprising a second elastic film body that covers and directly contacts a side of the another second space of the another communication hole so as to prevent a reverse flow of the fluid when the second elastic film body is in a second closed position;
an elastic member having a first elastic wall portion surrounding the communication hole and a second elastic wall portion surrounding the another communication hole for holding the first elastic film body and the second elastic film body; and
a nipping member for nipping the elastic member with the partition wall,
wherein a surface of the elastic member is closely attached to a surface on the side of the second space of the partition wall,
wherein a back surface on an opposite side of the surface is closely attached to the nipping member,
wherein the nipping member has a first protruding portion and a second protruding portion that protrude toward the partition wall,
wherein the first protruding portion is fitted into the second space surrounded by the first elastic wall portion so as to be in surface contact with the entire circumference of the first elastic wall portion to restrict positional displacement of the first elastic wall portion, so that deformation due to distortion of the first elastic film body and the first elastic wall portion is suppressed,
wherein the first protruding portion comprises a first ventilation passage that communicates with another first ventilation passage formed inside the nipping member,
wherein the second protruding portion is fitted into the another second space surrounded by the second elastic wall portion so as to be in surface contact with the entire circumference of the second elastic wall portion to restrict positional displacement of the second elastic wall portion, so that deformation due to distortion of the second elastic film body and the second elastic wall portion is suppressed, and wherein the first elastic wall portion, the second elastic wall portion, the first elastic film body, and the second elastic film body are integrated with the elastic member.

2. The check valve structure according to claim 1, wherein the elastic member is formed so that the first elastic wall portion has a larger thickness than the first elastic film body, and the second elastic wall portion has a larger thickness than the second elastic film body.

3. The check valve structure according to claim 1, wherein the second space and the another first space communicate with each other.

4. The check valve structure according to claim 1, wherein the first protruding portion and the first elastic wall portion are formed so as to have a size relationship in which the first protruding portion is pressed and fitted into the second space.

5. The check valve structure according to claim 1, wherein a surface facing the first elastic wall portion is chamfered in a protruding end of the first protruding portion.

6. A diaphragm pump for transporting gas by a capacity change of a pump chamber, comprising:
   a suction valve for bringing the gas into the pump chamber; and
   a discharge valve for bringing the gas out of the pump chamber,
   wherein the check valve structure according to claim 1 is used for at least one of the suction valve and the discharge valve.

7. A sphygmomanometer, comprising:
   a cuff attached to a blood pressure measuring site of a person to be measured, the cuff having a gas bag to be charged with gas;
   the diaphragm pump according to claim 6 for transferring the gas to the gas bag;
   a pressure detector for detecting pressure in the cuff; and
   a measuring unit for measuring blood pressure of the person to be measured from a pressure value detected by the pressure detector.

8. A diaphragm pump for transporting gas by a capacity change of a pump chamber, comprising:
   a suction valve for bringing the gas into the pump chamber; and
   a discharge valve for bringing the gas out of the pump chamber,
   wherein the check valve structure according to claim 2 is used for at least one of the suction valve and the discharge valve.

9. A diaphragm pump for transporting gas by a capacity change of a pump chamber, comprising:
   a suction valve for bringing the gas into the pump chamber; and
   a discharge valve for bringing the gas out of the pump chamber,
   wherein the check valve structure according to claim 3 is used for at least one of the suction valve and the discharge valve.

10. A diaphragm pump for transporting gas by a capacity change of a pump chamber, comprising:
    a suction valve for bringing the gas into the pump chamber; and
    a discharge valve for bringing the gas out of the pump chamber,
    wherein the check valve structure according to claim 4 is used for at least one of the suction valve and the discharge valve.

11. A diaphragm pump for transporting gas by a capacity change of a pump chamber, comprising:
    a suction valve for bringing the gas into the pump chamber; and
    a discharge valve for bringing the gas out of the pump chamber,
    wherein the check valve structure according to claim 5 is used for at least one of the suction valve and the discharge valve.

12. A sphygmomanometer, comprising:
    a cuff attached to a blood pressure measuring site of a person to be measured, the cuff having a gas bag to be charged with gas;
    the diaphragm pump according to claim 8 for transferring the gas to the gas bag;
    a pressure detector for detecting pressure in the cuff; and
    a measuring unit for measuring blood pressure of the person to be measured from a pressure value detected by the pressure detector.

13. A sphygmomanometer, comprising:
    a cuff attached to a blood pressure measuring site of a person to be measured, the cuff having a gas bag to be charged with gas;
    the diaphragm pump according to claim 9 for transferring the gas to the gas bag;
    a pressure detector for detecting pressure in the cuff; and
    a measuring unit for measuring blood pressure of the person to be measured from a pressure value detected by the pressure detector.

14. A sphygmomanometer, comprising:
    a cuff attached to a blood pressure measuring site of a person to be measured, the cuff having a gas bag to be charged with gas;
    the diaphragm pump according to claim 10 for transferring the gas to the gas bag;
    a pressure detector for detecting pressure in the cuff; and
    a measuring unit for measuring blood pressure of the person to be measured from a pressure value detected by the pressure detector.

15. A sphygmomanometer, comprising:
    a cuff attached to a blood pressure measuring site of a person to be measured, the cuff having a gas bag to be charged with gas;
    the diaphragm pump according to claim 11 for transferring the gas to the gas bag;
    a pressure detector for detecting pressure in the cuff; and
    a measuring unit for measuring blood pressure of the person to be measured from a pressure value detected by the pressure detector.

* * * * *